United States Patent
Wulff

(10) Patent No.: US 10,912,953 B2
(45) Date of Patent: Feb. 9, 2021

(54) ADAPTIVE PENCIL BEAM SCANNING

(71) Applicant: Varian Medical Systems Particle Therapy GmbH, Troisdorf (DE)

(72) Inventor: Joerg Wulff, Krefeld (DE)

(73) Assignee: Varian Medical Systems Particle Therapy GMBH, Troisdorf (DE)

(*) Notice: Subject to any disclaimer, the term of this patent is extended or adjusted under 35 U.S.C. 154(b) by 756 days.

(21) Appl. No.: 15/087,292

(22) Filed: Mar. 31, 2016

(65) Prior Publication Data

US 2017/0281980 A1    Oct. 5, 2017

(51) Int. Cl.
| | | |
|---|---|---|
| *A61N 5/10* | (2006.01) | |
| *G21K 1/10* | (2006.01) | |
| *G21K 5/04* | (2006.01) | |
| *G21K 1/093* | (2006.01) | |
| *H01J 37/08* | (2006.01) | |
| *H01J 37/14* | (2006.01) | |

(52) U.S. Cl.
CPC .......... *A61N 5/1077* (2013.01); *A61N 5/1043* (2013.01); *G21K 1/093* (2013.01); *G21K 1/10* (2013.01); *G21K 5/04* (2013.01); *H01J 37/08* (2013.01); *H01J 37/14* (2013.01); *A61N 2005/1087* (2013.01); *A61N 2005/1095* (2013.01); *H01J 2237/14* (2013.01)

(58) Field of Classification Search
None
See application file for complete search history.

(56) References Cited

U.S. PATENT DOCUMENTS

| | | |
|---|---|---|
| 4,958,078 A | 9/1990 | Becchetti |
| 6,777,700 B2 | 8/2004 | Yanagisawa et al. |
| 7,385,203 B2 | 6/2008 | Nakayama et al. |
| 2004/0104354 A1 | 6/2004 | Haberer et al. |
| 2006/0226372 A1 | 10/2006 | Yanagisawa et al. |
| 2009/0202045 A1* | 8/2009 | Guertin ............... A61N 5/10 378/195 |
| 2009/0242789 A1* | 10/2009 | Tachikawa ........... A61N 5/10 250/396 R |

(Continued)

FOREIGN PATENT DOCUMENTS

| | | |
|---|---|---|
| CN | 1161240 | 10/1997 |
| CN | 1997256 | 7/2007 |

(Continued)

*Primary Examiner* — Kaylee R Wilson

(57) ABSTRACT

Embodiments of the present invention disclose methods and systems for producing an adaptive pencil beam having an adjustable lateral beam size and Bragg-peak width. According to one disclosed embodiment, an apparatus for producing an adaptive pencil beam is disclosed. The apparatus includes a set of momentum band expanders configured to widen a momentum spread of a pencil beam, where a momentum band expander is selected from the set of momentum band expanders to receive the pencil beam, and a slit at dispersive focus of two dipole magnets to adjust a width of a Bragg-peak of the pencil beam. According to another disclosed embodiment, a method for producing an adaptive pencil beam with an adjustable lateral beam is disclosed. The method includes selecting a scatter foil, or setting of a defocusing/focusing magnet, and adjusting a lateral size of the pencil beam.

24 Claims, 7 Drawing Sheets

(56) References Cited

U.S. PATENT DOCUMENTS

| | | | |
|---|---|---|---|
| 2010/0054413 A1* | 3/2010 | Sobering | G06F 19/3481 |
| | | | 378/65 |
| 2010/0243921 A1 | 9/2010 | Flynn et al. | |
| 2011/0101235 A1 | 5/2011 | Iwata | |
| 2011/0240874 A1 | 10/2011 | Iwata | |
| 2012/0280150 A1* | 11/2012 | Jongen | A61N 5/10 |
| | | | 250/492.3 |
| 2014/0091734 A1 | 4/2014 | Gall et al. | |
| 2015/0031933 A1* | 1/2015 | Yamamoto | A61N 5/1043 |
| | | | 600/1 |
| 2015/0087887 A1 | 3/2015 | Iwata | |
| 2017/0157426 A1* | 6/2017 | Buchsbaum | A61N 5/1031 |

FOREIGN PATENT DOCUMENTS

| | | | |
|---|---|---|---|
| CN | 101763909 A * | 6/2010 | |
| CN | 103794261 | 5/2014 | |
| EP | 0826394 | 3/1998 | |
| JP | H1151310 | 6/1999 | |

* cited by examiner

ADAPTIVE PENCIL BEAM SCANNING

FIELD

Embodiments of the present invention generally relate to the field of particle therapy by means of pencil-beam scanning. More specifically, embodiments of the present invention relate to systems and methods for performing adaptive pencil beam scanning using pencil beams with spot sizes of different lateral sizes and with variable widths in depth.

BACKGROUND

Standard radiation therapy using X-ray beams deposit their energy along the path of the beam to a target tumor. However, the reach of the energy also extends beyond the target tumor, and may deliver radiation to healthy tissue around the tumor site. This excess radiation may damage normal tissue or organs near the target area.

Particle therapy with protons or other ions is a type of radiotherapy that uses an external beam to provide targeted ionizing radiation to a tumor. Protons or other positively charged ions are sent to an accelerator to bring the particles' energy to a predetermined value. The protons or other ions then move through a beam-transport system, where magnets are used to shape, focus and/or direct the proton or other ion beam as necessary.

Particle therapy by means of pencil beam scanning offers a high degree of freedom to shape the resulting dose distribution to target volumes and to avoid adjacent organs. Applying a dose with maximum conformity generally requires a narrow lateral beam size and a sharp distal fall-off in depth. However, the smaller the beam size, both laterally and in depth, the more spatially distributed points need to be reached using changed energy layers and lateral positions of individual proton or ion pencil beams. This leads to prolonged beam delivery times and potentially lowers robustness of treatments, in some cases, due to interplay effects in moving targets.

SUMMARY

Methods and systems for producing an adaptive pencil beam having an adjustable lateral beam size and Bragg-peak width are disclosed herein.

According to one disclosed embodiment, an apparatus for producing an adaptive pencil beam Bragg-peak width is disclosed. The apparatus includes a set of momentum band expanders configured to widen a momentum spread of a pencil beam, where a momentum band expander is selected from the set of momentum band expanders to receive the pencil beam, a slit at a dispersive focus of a set of dipoles, where the slit is configured to adjust the momentum band and width of a Bragg-peak of the pencil beam, and an adjustment element configured to adjust a lateral size of the pencil beam.

According to another disclosed embodiment, a method for producing an adaptive pencil beam having an adjustable lateral beam size and Bragg-peak width is disclosed. The method includes selecting a momentum band expander from a set of momentum band expanders, receiving a pencil beam at the momentum band expander, widening a momentum spread of the pencil beam using the momentum band expander, and passing the pencil beam through a slit to adjust the width of a Bragg-peak of the pencil beam.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION

Figure 1:
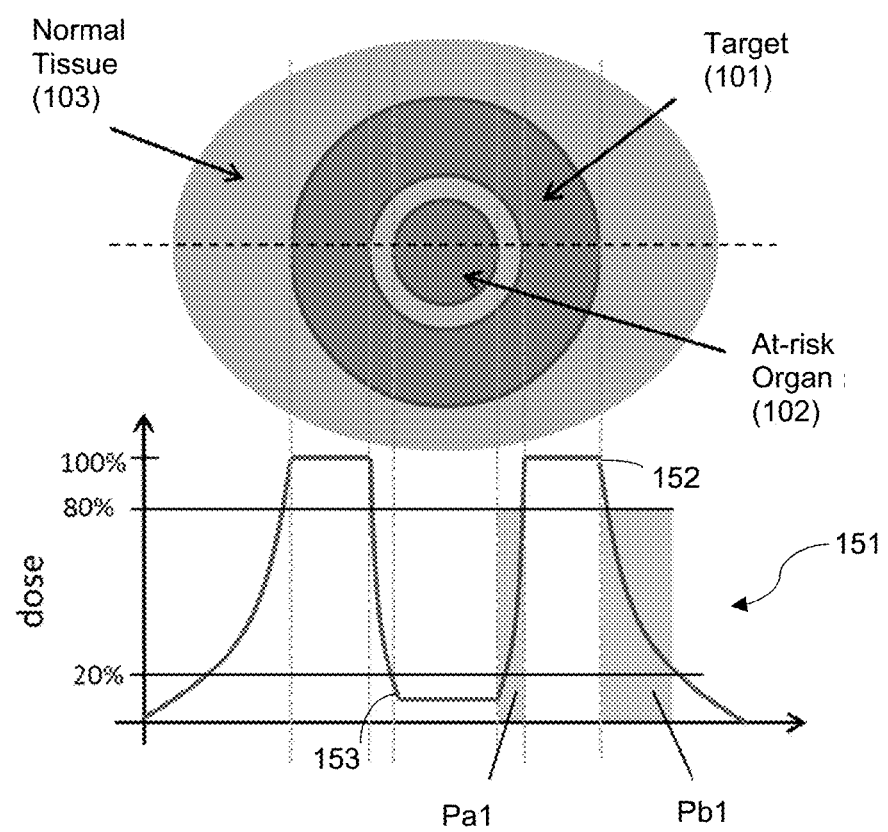
FIG. 1 is a diagram depicting an exemplary target volume shape and an at-risk organ in close proximity.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, components, and circuits have not been described in detail as not to unnecessarily obscure aspects and features of the subject matter.

Portions of the detailed description that follows are presented and discussed in terms of a method. Although steps and sequencing thereof are disclosed in a figure herein describing the operations of this method, such steps and sequencing are exemplary. Embodiments are well suited to performing various other steps or variations of the steps recited in the flowchart (e.g., FIG. 5A) of the figures herein, and in a sequence other than that depicted and described herein.

Some portions of the detailed description are presented in terms of procedures, steps, logic blocks, processing, and other symbolic representations of operations on data bits that can be performed on computer memory. These descriptions and representations are the means used by those skilled in the data processing arts to most effectively convey the substance of their work to others skilled in the art. A procedure, computer-executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "accessing," "writing," "including," "storing," "transmitting," "traversing," "associating," "identifying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Some embodiments may be described in the general context of computer-executable instructions, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Adaptive Pencil Beam Scanning

The following description is presented to enable a person skilled in the art to make and use the embodiments of this invention; it is presented in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present invention is not limited to the embodiments shown, but is to be accorded the widest scope consistent with the principles and features disclosed herein.

FIG. 1 illustrates an exemplary target volume shape 101 and an at-risk organ 102 in close proximity. The lower portion of FIG. 1 is a graph illustrating an exemplary dose prescription scheme 151, where the maximum dose 152 is required within the target, and the dose 153 is required outside the target. The dose provided to an at-risk radiosensitive organ needs to be minimized, resulting in a need for a steep gradient, characterized by the penumbra PA1. For other normal tissue that is not an organ at-risk 103, the dose needs to be minimized as well, but the dose gradient may be lower, characterized by penumbra Pb1. In pencil beam scanning the dose distribution is constructed from individual beams optimized in a treatment planning system to meet requirements of the distribution as much as possible. In general, the smaller the 'spot'(both laterally and in depth) the higher the conformity, meaning organs at risk are less exposed. When a greater number of spots are used, the treatment lasts longer and the probability for interplay effects is increased. However, when the computerized treatment planning system is configured to adapt the underlying pencil beams by selection from a library of beams of different size, both laterally and in terms of width in depth, a large degree of conformity of planned distributions van be expected with a minimized number of individual beams, and thus minimized penalty on overall treatment time.

Figure 2A:
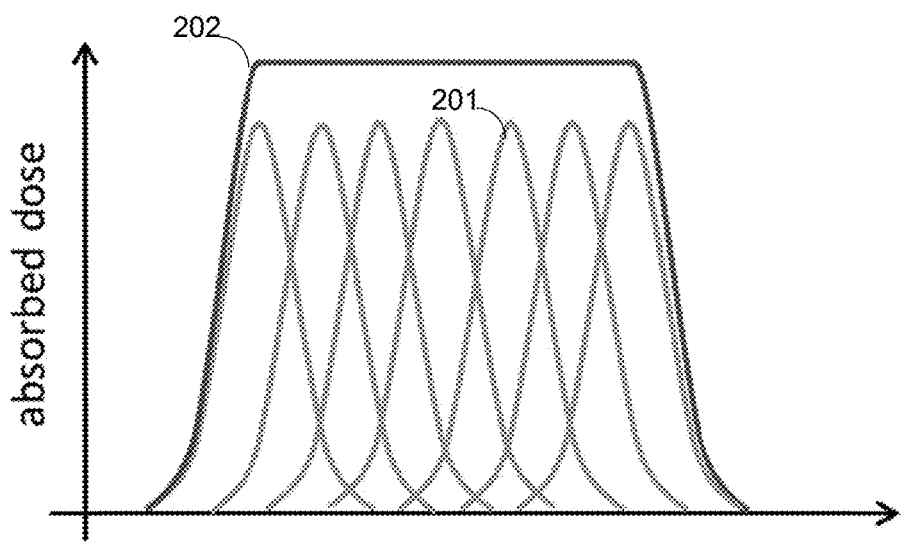
FIG. 2A is a graph depicting an exemplary superposition of a single pencil beam shape producing a laterally extended field according to embodiments of the present invention.

With regard to FIG. 2A, an exemplary superposition of a beam having a single spot shape 201 producing a laterally extended, homogenous dose distribution 202 is depicted according to embodiments of the present invention. The vertical axis indicates the amount of absorbed dosage. The lateral penumbra of a dose distribution is dictated by the shape of the single underlying approximately Gaussian pencil beam shape. When using a single spot size, the size defines the lower limits of the lateral penumbra. When variable spot sizes are selected to form the required dose distribution, the spots may be used more efficiently meaning there are high gradients only where necessary, and the overlap of large spots reduces susceptibility to motion.

Figure 2B:
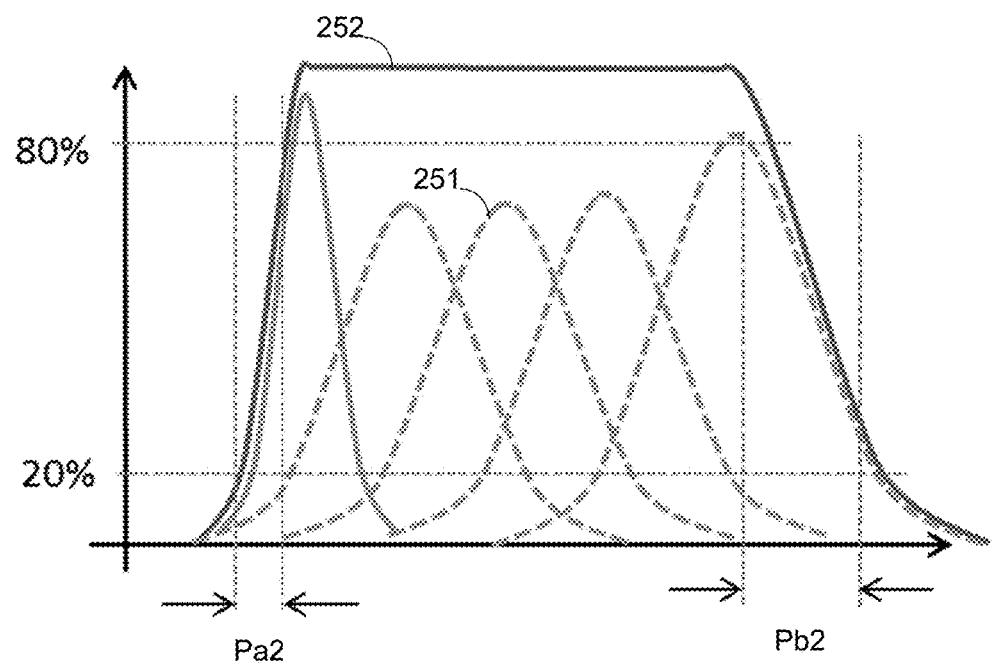
FIG. 2B is a graph depicting au exemplary lateral dose distribution produced by magnetic defocusing or a scattering element in the path of individual pencil beams according to embodiments of the present invention.

According to embodiments of the present invention, a lateral beam size 251 may be increased by magnetic defocusing or by using a scattering element are the path of the individual pencil beams, for example, resulting in the exemplary distribution 252 depicted in FIG. 2B. Once again, the dose provided to an at-risk radiosensitive organ must be minimized, resulting in a need for a steep gradient, characterized by the penumbra Pa2The dose gradient may be lower for other non-target normal tissue, characterized by the penumbra Pb2. Instead of using spots of different sizes one-by-one, a single energy layer can be split to sub-layers with different spot sizes and subsequently applied to the target. According to some embodiments, a collimator is used to narrow the pencil beam and adjust the spot size.

Figure 3A:
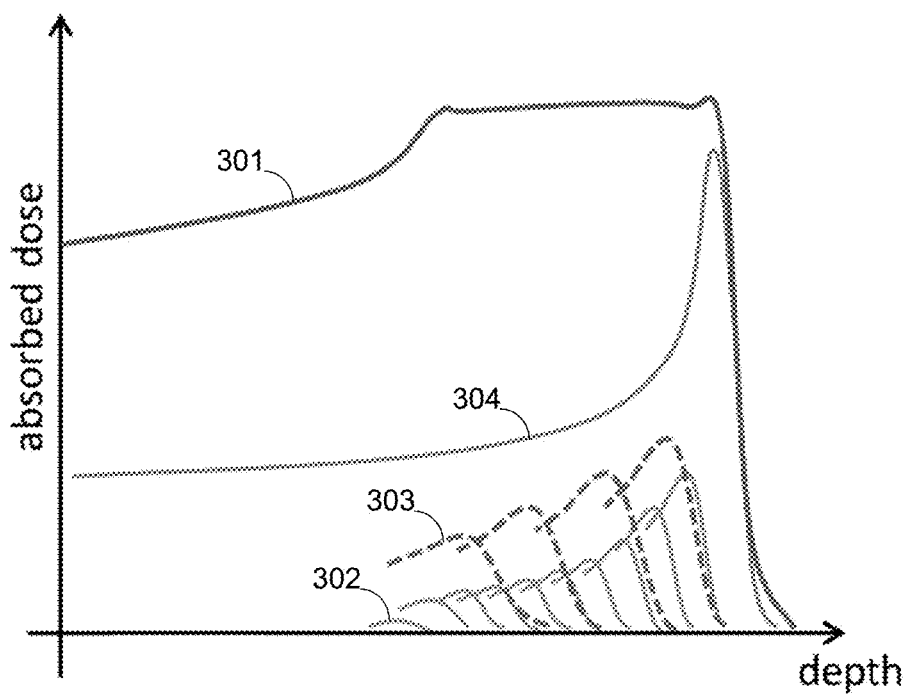
FIG. 3A is a graph depicting an exemplary spread-out Bragg peak distribution in depth constructed from individual beams of different energies according to embodiments of the present invention.
Figure 3B:
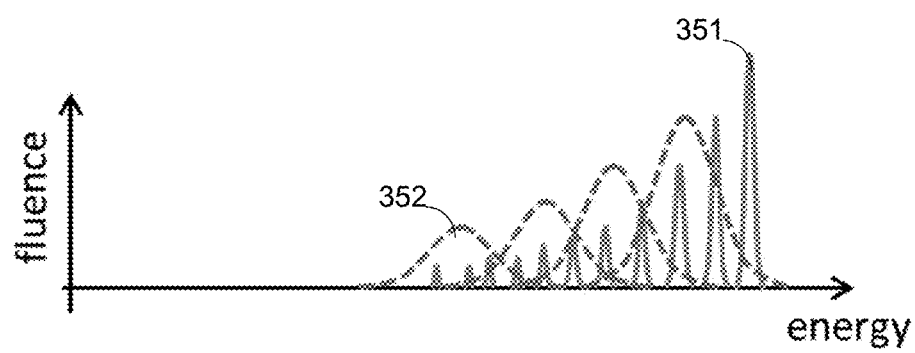
FIG. 3B is a graph depicting the width of an exemplary single Bragg-peak defined by the energy spread around the mean energy/range, according to embodiments of the present invention.

With regard to FIG. 3A, an exemplary spread-out Bragg peak 301 constructed from individual beams of different energy 302 is depicted according to embodiments of the present invention. The distribution of the dose in depth is constructed using overlapping Bragg-peaks, and the width of the most distal Bragg-peak 304 defined the distal fall-off. The broken lines 303 represent underlying Brag-peaks for a widened energy spread. Within the direction of the pencil beam, the Bragg-peak still exhibits a steep dose fall-off. The broader the individual beams, the less energy and layers are required to achieve the homogeneous dose plateau. FIG. 3B depicts the width 351 of an exemplary single Bragg-peak 352, defined by the energy spread around the mean energy/range, according to embodiments of the present invention.

According to some embodiments, ripple/ridge filter may be used as momentum band expanders to broaden the width of a single Bragg-peak. Ripple filters are usually placed close to the patient to avoid unnecessary lateral scattering. When the momentum band expander is included as part of the energy degrading and selection system, the subsequent beam-optics elements may still lead to a small and laterally defined pencil beam. When the beam-line optics are optimized for larger acceptance, a momentum band expander may be used to broaden the momentum band (e.g., energy spread) for a desired Bragg-peak shape as defined by treatment planning optimization.

According to some embodiments, a library of lateral spot sizes may be produced using an adjustment element, for example, magnetic focusing/defocusing or a variable thickness scatterer.

According to some embodiments, the treatment planning system optimizes the delivery to take higher degrees of freedom into account and adapts the dose distribution by selecting the individual underlying pencil beams from the library according to required lateral and distal fall-offs.

Figure 4A:
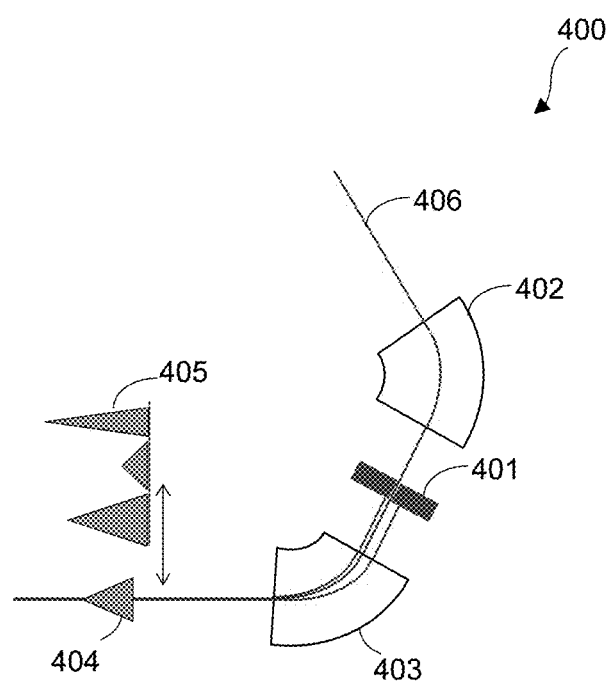
FIG. 4A is a diagram depicting an exemplary apparatus for shaping a pencil beam Bragg-peak width using momentum band expanders according to embodiments of the present invention.

With regard to FIG. 4A, a diagram of an exemplary apparatus 400 for generating a pencil beam 406 with variable Bragg-peak width using a momentum band expander 404 is depicted according to embodiments of the present invention. The momentum band expander 404 is selected from a set of momentum band expanders 405 and widens the momentum spread for the beam 406 of a proton or other ion source at a given energy. A slit 401 at the dispersive focus between a set of two dipole magnets 402 and 403 is adjusted to limit the width of the spread. Adjusting the energy slit 401 allow the modulation of the spread during treatment of a single energy layer.

According to some embodiments, apparatus 400 does not include slits, and the beam width is less focused and/or larger in diameter. Quad magnets (not pictured) are used to adjust and/or focus the beam. The quad magnets may be adjusted as desired to narrow the width of the beam for providing treatment.

Figure 4B:
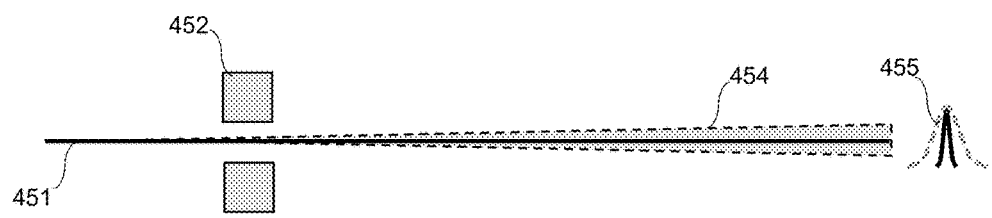
FIG. 4B is a diagram depicting an exemplary apparatus for adjusting the lateral size of a pencil beam using magnets according to embodiments of the present invention.

With regard to FIG. 4B, an exemplary apparatus for adjusting the lateral size of a pencil beam using magnets is depicted according to embodiments of the present invention. The apparatus includes magnets 452 with variable field strength for adjusting a lateral size of incident proton or other ion beam 451. According to some embodiments, magnets 452 comprise focusing and de-focusing quadropole magnets. Variable lateral beam size 455 and corresponding beam envelope 454 of incident proton or other ion beam 451 may be adjusted using magnets 452.

Figure 4C:
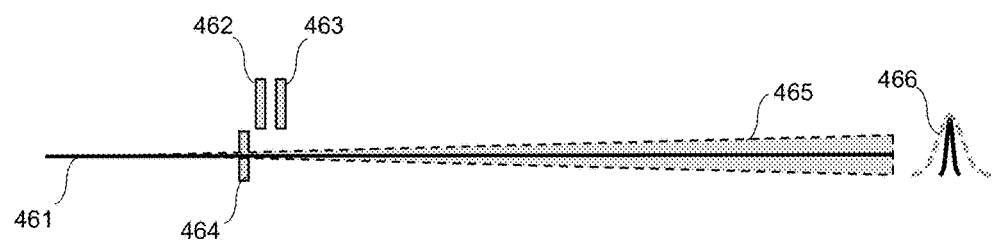
FIG. 4C is a diagram depicting an exemplary apparatus for adjusting the lateral size of a pencil beam using variable thickness scatterers according to embodiments of the present invention.

With regard to FIG. 4C an exemplary apparatus for adjusting the lateral size of a pencil beam using variable thickness scatterers is depicted according to embodiments of the present invention. The apparatus includes variable thickness scatterers 462-464 for adjusting a lateral size of incident proton or other ion beam 461. One of the variable thickness scatterers 462-464 (e.g., variable thickness scatterer 464) is placed in the path of incident proton or other ion beam 461. Variable lateral beam size 466 and corresponding beam envelope 465 of incident proton or other ion beam 461 may be adjusted using variable thickness scatterers 462-464.

Figure 5A:
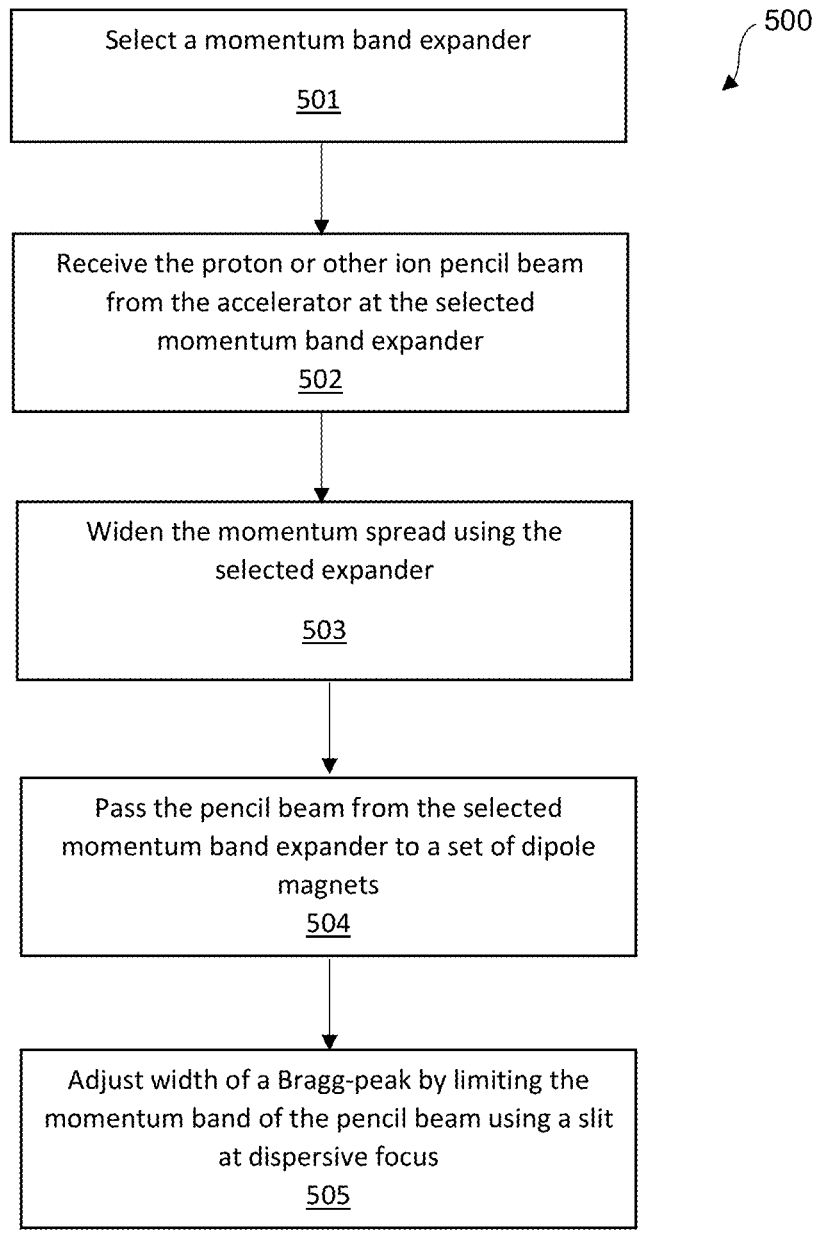
FIG. 5A is a flow-chart depicting an exemplary sequence steps for performing a method of producing an adaptive pencil beam width in depth according to embodiments of the present invention.

With regard to FIG. 5A, a flowchart 500 of an exemplary sequence of steps for producing a pencil beam with variable width in depth is depicted according to embodiments of the present invention. At step 501, a momentum band expander is selected from a set of momentum band expanders. At step 502, a pencil beam (e.g., a proton or other ion pencil beam) is received from the accelerator at the selected momentum band expander. At step 503, the selected momentum band expander widens a momentum spread of the pencil beam. At step 504, the pencil beam is passed from the selected momentum band expander to a set of dipole magnets. At step 505, a width of a Bragg-peak is adjusted by limiting the momentum band of the pencil beam using a slit at dispersive focus.

Figure 5B:
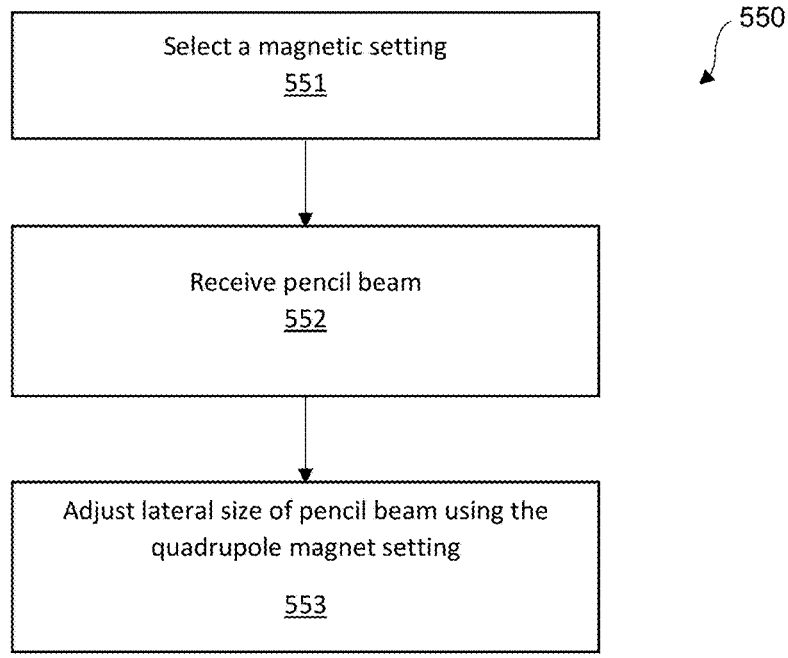
FIG. 5B is a flow-chart depicting an exemplary sequence steps for performing a method of adjusting a lateral size of an adaptive pencil beam using magnets according to embodiments of the present invention.

With regard to FIG. 5B, a flowchart of an exemplary sequence of steps 550 for producing a pencil beam with variable lateral size by means of magnetic focusing/defocusing is depicted according to embodiments of the present invention. At step 551, a magnetic setting is selected. At step 552, a pencil beam is received at the magnet. At step 553, the magnet adjusts the lateral size of the pencil beam.

Figure 5C:
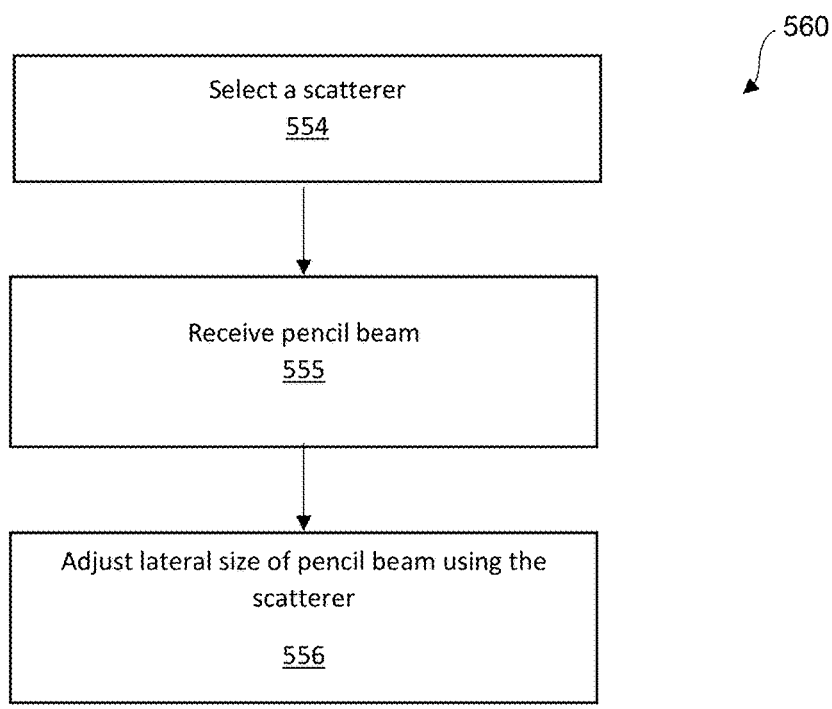
FIG. 5C is a flow-chart depicting an exemplary sequence steps for performing a method of adjusting a lateral size of an adaptive pencil beam using a scatterer according to embodiments of the present invention.

With regard to FIG. 5C, a flowchart of an exemplary sequence of steps 560 for producing a pencil beam with a variable lateral size using scatterers is depicted according to embodiments of the present invention. At step 554, a scatterer is selected. At step 555, a pencil beam is received at the scatterer. At step 556, the scatterer adjusts the lateral size of the pencil beam.

Embodiments of the present invention are thus described. While the present invention has been described in particular embodiments, it should be appreciated that the present invention should not be construed as limited by such embodiments, but rather construed according to the following claims.

What is claimed is:

1. A method for producing adaptive pencil beams comprising:
    selecting a first momentum hand expander from a set of momentum hand expanders;
    widening a momentum spread of a proton or ion beam using the first momentum band expander to generate at least one pencil beam having a first momentum spread;
    selecting a second momentum band expander from the set of momentum band expanders;
    widening the momentum spread of the proton or ion beam using the second momentum band expander to, generate at least one pencil beam having a second momentum spread;
    passing the proton or ion beam including the at least one pencil beam having the first momentum spread and the at least one pencil beam having the second momentum, spread through a slit to limit the momentum spread of the proton or ion beam including the at least one pencil beam having the first momentum spread and the at least one pencil beam having the second momentum spread;
    adjusting a lateral size of the proton or ion beam to further generate at least pencil beam having a first lateral width and at least one pencil beam having a second lateral width; and
    wherein superposition of a plurality of pencil beams including the at least one pencil beam having the first momentum spread and the at least one pencil beam having the second momentum spread is characterized by a first lateral fall-off based on the at least one pencil beam having the first lateral width and a second lateral fall-off based on the at least one pencil beam having the second lateral width and by a first distal fall-off based on the at least one pencil beam having the first momentum spread and a second distal fall-off based on the at least one pencil beam having the second momentum, spread.

2. The method of claim 1, further comprising:
    selecting a magnet setting;
    receiving the proton or ion beam at a magnet focusing element, wherein the magnet focusing element is configured using the magnet setting, and
    wherein the adjusting comprises adjusting the lateral size of the proton or ion beam using the magnet focusing element, wherein the magnetic focusing element is configured to perform at least one of magnetic focusing and magnetic de-focusing.

3. The method of claim 2, further comprising:
selecting a scatterer thickness;
receiving the proton or ion beam at a scatterer, wherein the scatter is configured based on the scatterer thickness, and
wherein the adjusting further comprises adjusting the lateral size of the proton or ion beam using the scatterer.

4. The method of claim 3, further comprising storing a set of pencil beam shapes in a library of pencil beam shapes, wherein the momentum band expander, the slit and an adjustment element configured to adjust the lateral size of the proton or ion beam are automatically adjusted when a first pencil beam shape is selected from the library of pencil beam shapes, wherein the adjustment element comprises the magnet focusing element or the scatterer or both.

5. The method of claim 4, wherein the library of pencil beam shapes comprises pencil beam shapes having different lateral sizes and momentum spreads.

6. The method of claim 5, wherein a different pencil beam shape may be automatically selected from the library of pencil beam shapes to increase a degree of conformity of a planned dose distribution.

7. The method of claim 2, further comprising storing a set of pencil beam shapes in a library of pencil beam shapes, wherein the momentum band expander, the slit and the magnet focusing element are automatically adjusted when a first pencil beam shape is selected from the library of pencil beam shapes.

8. The method of claim 1, wherein the slit is at a dispersive focus between first and second dipole magnets.

9. A computer program product tangibly embodied in a computer-readable storage device and comprising instructions that when executed by a processor perform a method for producing adaptive pencil beams comprising:
selecting a first momentum band expander from a set of momentum band expanders;
widening a momentum spread of a proton or ion beam using the first momentum band expander to generate at least one pencil beam having a first momentum spread;
selecting a second momentum hand expander from the set of momentum band expanders;
widening the momentum spread of the proton or ion beam using the second momentum band expander to generate at least one pencil beam having a second momentum spread;
passing the proton or ion beam including the at least one pencil beam having the first momentum spread and the at least one pencil beam having the second momentum spread through a slit to limit the momentum spread of the proton or ion beam including the at least one pencil beam having the first momentum spread and the at least one pencil beam having the second momentum spread;
adjusting a lateral size of the proton or ion beam to further generate at least one pencil beam having a first lateral width and at least, one pencil beam having a second lateral width; and
wherein superposition of a plurality of pencil beams including the at least one pencil beam having the first momentum spread and the at least one pencil beam having the second momentum spread is characterized by a first lateral fall-off based on the at least one pencil beam having the first lateral width and a second lateral fall-off based on the at least one pencil beam having the second lateral width and by a first distal fall-off based on the at least one pencil beam having the first momentum spread and a second distal tall-off based on the at least one pencil beam having the second momentum spread.

10. The computer program of claim 9, wherein the method further comprises;
selecting a magnet setting;
receiving the proton or ion beam at a magnet focusing element, wherein the magnet focusing element is configured using the magnet setting, and
wherein the adjusting comprises adjusting the lateral size of the proton or ion beam using the magnet focusing element, wherein the magnetic focusing element is configured to perform at least one of magnetic focusing and magnetic de-focusing.

11. The computer program of claim 10, wherein the method further comprises storing a set of pencil beam shapes in a library of pencil beam shapes, wherein the momentum band expander, the slit and the magnet focusing element are automatically adjusted when a first pencil beam shape is selected from the library of pencil beam shapes.

12. The computer program of claim 9, wherein the method further comprises;
selecting a scatterer thickness;
receiving the proton or ion beam at a scatterer, wherein the scatter is configured based on the scatterer thickness, and
wherein the adjusting further comprises adjusting the lateral size of the proton or ion beam using the scatterer.

13. The computer program of claim 12, wherein the method further comprises storing a set of pencil beam shapes in a library of pencil beam shapes, wherein the momentum band expander, the slit and the scatterer are automatically adjusted when a first pencil beam shape is selected from the library of pencil beam shapes.

14. The computer program of claim 13, wherein the method further comprises storing a set of different distal fall-offs in the library of pencil beam shapes, wherein the different distal fall-offs are produced using the set of momentum band, expanders.

15. The computer program of claim 9, wherein the method further comprises selecting a beam shape based on motion information.

16. The computer program of claim 9, wherein the slit is at a dispersive focus between first and second dipole magnets.

17. A method for producing adaptive pencil beams comprising:
receiving a proton or ion beam;
adjusting a lateral size/width of the proton or ion beam to generate a plurality of pencil beams including a least one pencil beam of a first lateral width and at least one pencil beam of a second lateral width;
adjusting a momentum spread of the proton or ion beam to further generate the plurality of pencil beams including at least one pencil beam of a first momentum spread and at least one pencil beam of a second momentum spread; and
wherein superposition of the plurality of pencil beams is characterized by first lateral fall-off based on the at least one pencil beam of the first lateral width and a second lateral fall-off based on the at least one pencil beam of the second lateral width and by first distal fall-off based on the at least one pencil beam of the first momentum spread and a second distal fall-off based on the at least one pencil beam of the second momentum spread.

18. The method of claim 17, wherein the momentum spread of the proton or ion beam is adjusted using a set of momentum band expanders.

19. The method of claim 18, wherein the set of momentum band expanders comprise a ripple/ridge.

20. The method of claim 18, wherein the momentum spread of the proton or ion beam is further adjusted using an energy slit to limit the momentum spread of the plurality of pencil beams.

21. The method of claim 20, wherein the energy slit is located at a dispersive focus location along the proton or ion beam.

22. The method of claim 17, wherein the lateral size/width of the pencil beam is adjusted using magnetic focusing/defocusing.

23. The method of claim 22, wherein the magnetic focusing/defocusing comprise a quadrupole magnet.

24. The method of claim 17, wherein the lateral size/width of the pencil beam is adjusted using variable thickness scatterers.

* * * * *